United States Patent [19]

Weisenborn et al.

[11] 4,296,101
[45] Oct. 20, 1981

[54] ANTIBIOTIC KRISTENIN

[75] Inventors: Frank L. Weisenborn, Titusville; William E. Brown, Princeton; Edward Meyers, East Brunswick, all of N.J.

[73] Assignee: E. R. Squibb & Sons, Inc., Princeton, N.J.

[21] Appl. No.: 877,199

[22] Filed: Feb. 13, 1978

[51] Int. Cl.$^3$ .................... A61K 35/00; C12P 13/00; C12P 1/04; C12R 1/125
[52] U.S. Cl. .................................. 424/119; 435/128; 435/129; 435/170; 435/253; 435/839
[58] Field of Search ................ 424/119; 435/128, 129, 435/170, 253, 839

[56] References Cited

U.S. PATENT DOCUMENTS 3,282,794  11/1966  Okumura et al. .................... 435/244
3,843,784  10/1974  Hamill et al. ........................ 424/119

FOREIGN PATENT DOCUMENTS 722433   1/1955  United Kingdom ................ 435/839
785449  10/1957  United Kingdom ................ 435/839

OTHER PUBLICATIONS

Ryosaku Takeda et al., "Antimicrobial Activity of Bacillus subtilis, I. Influence of Antimicrobial Activity on the Growth of Yeast in Soy Sauce," Chem. Absts., vol. 67, No. 9, p. 3977, (1967), Abs. No. 42545v.
Shoji et al., "Isolation of a New Peptide Antibiotic TL-119, Antibiotics from the genus Bacillus, IV", Chem. Absts., vol. 83, No. 3, p. 86, (1975), Abs. No. 22893j.
Ichihashi et al., "Antibiotic A-3302-A and -B", Chem. Absts., vol. 85, No. 1, p. 317, (1976), Abs. No. 3872b.
Magno et al., "Antibiotic from a Spore-Forming Bacteria", Chem. Absts., vol. 84, No. 1, p. 296, (1976), Abs. No. 3244c.
Okazaki et al., "A New Antibiotic Baciphelacin", J. Antibiotics, vol. XXVII, No. 9, (1975), pp. 717-719.

Primary Examiner—Thomas G. Wiseman
Attorney, Agent, or Firm—Lawrence S. Levinson; Stephen B. Davis

[57] ABSTRACT

A new antibiotic, designated kristenin, is produced by the microorganism Bacillus subtilis. The antibiotic possesses activity against gram positive bacteria.

4 Claims, 1 Drawing Figure

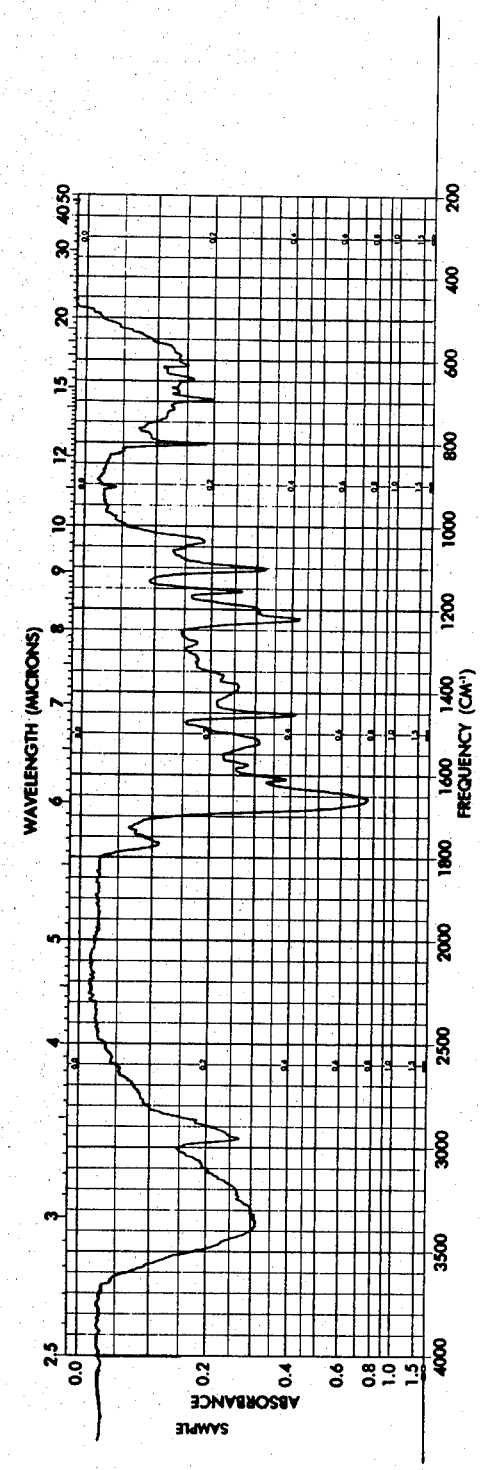

ized bacimethod for its production. The antibi-

ANTIBIOTIC KRISTENIN

BACKGROUND OF THE INVENTION

Okazaki et al. in the *Journal of Antibiotics*, Vol. 28, No. 9, pages 717-719, describe the preparation of an antibiotic designated baciphelacin. This antibiotic is stated to be active against gram positive bacteria. Baciphelacin and kristenin are members of the same family of antibiotics.

SUMMARY OF THE INVENTION

This invention relates to a new antibiotic designated kristenin, and to a method for its production. The antibiotic is obtained by cultivating the microorganism *Bacillus subtilis* ATCC 31340 in an aqueous nutrient medium comprising an assimilable carbohydrate and an assimilable nitrogen source under submerged aerobic conditions until substantial antibiotic activity is imparted to the medium.

The fermentation broth is filtered and the filtrate extracted with a water immiscible chlorinated solvent such as dichloroethane. The antibiotic is extracted from the aqueous phase with a water immiscible alcohol, preferably n-butanol. The alcoholic solution is concentrated and the product purified by absorption on a cation exchange resin followed by elution with dilute acid. The eluate is neutralized and the bioactive material again extracted into butanol. The butanol extract is concentrated to yield the crude antibiotic, designated kristenin, that may be further purified by preparative thin layer chromatography on silica gel using an alcohol-water-organic acid system, e.g. butanol-water-acetic acid. Final purification is accomplished by chromatography on Sephadex LH20 followed by preparative high performance liquid chromatography (HPLC) and precipitation from isopropanol-hexane.

The invention is also directed to a biologically pure culture of the microorganism *Bacillus subtilis* ATCC 31340 which is capable of producing the antibiotic kristenin in recoverable amounts.

The FIGURE shows the infrared spectrum of antibiotic kristenin in KBr.

DETAILED DESCRIPTION OF THE INVENTION

The Microorganism

The microorganism useful for the preparation of kristenin is a species of Bacillus hereinafter designated *Bacillus subtilis* ATCC 31340.

Microscopic:

Spore-forming, gram positive bacillus. The spores are central to subcentral and just barely distend the sporangial wall. Vegetative cells, grown on glucose agar (soil extract agar with 1% glucose) stain uniformly with crystal violet (5–10 sec.). The vegetative cells are motile. The growth temperature range in nutrient broth is between 13°–45° C.

Physiological Characters:

The organism produces catalase; gives a positive Voges-Proskauer test for production of acetylmethylcarbinol; pH in Voges-Proskauer broth is 5; grows in 7% sodium chloride; grows at pH 5.7; hydrolyzes starch, utilizes citrate on Simmon's citrate agar; decomposes casein.

*Bacillus subtilis* ATCC 31340 does not grow under anaerobic conditions. It utilizes glucose and mannitol as a sole carbon source in an inorganic medium, but cannot utilize arabinose or xylose under these conditions.

These characteristics agree with those of *Bacillus subtilis* ATCC 15,562 in all the essential characters and serve to identify the producer of kristenin as *Bacillus subtilis*.

Production of the Antibiotic

*Bacillus subtilis* ATCC 31340 produces an antibiotic that possesses activity against gram positive bacteria. To form the antibiotic, *Bacillus subtilis* ATCC 31340 is grown at about 25° C. under submerged aerobic conditions in an aqueous nutrient medium containing assimilable carbon and nitrogen sources. The fermentation is carried out for approximately 15–72 hours, preferably about 40 hours, at the end of which time the antibiotic has been formed.

After the fermentation is completed, the suspension is centrifuged. The supernate is first extracted with dichloroethane to remove lipophilic material. The pH is adjusted to 7.5 and the antibiotic is extracted from the aqueous phase with butanol. The butanol extract is concentrated under vacuum, and the residue is dissolved in 30% methanol-water solution and treated batch-wise with Amberlite CG-50 ($H^+$) ion exchange resin. The resin is transferred to a column, washed successively with 30% methanol and 80% methanol, and finally the antibiotic is eluted with 0.1 N hydrochloric acid in 30% methanol-water. The combined bioactive fractions are concentrated to remove the methanol, adjusted to pH 7.7 with 2 N sodium hydroxide, and extracted with butanol. The butanol extracts are washed with water and concentrated under vacuum to yield crude antibiotic.

The antibiotic is further purified by perparative thin layer chromatography on silica gel using the upper phase of the solvent system, butanol-acetic acid-water (8:1:10). The band centered at Rf of 0.47 contains the bioactive substance and is eluted from the silica gel with the solvent mixture used for development. Additional purification is accomplished by gel filtration through Sephadex LH-20 eluting with 0.5% acetic acid in 80% methanol. Final purification is achieved by preparative high performance liquid chromatography on Porasil using the upper phase of the solvent system butanol-acetic acid-water (8:1:10) that is further diluted by 10% of its volume of butanol. The combined bioactive fractions are concentrated to dryness and the amorphous antibiotic so obtained is precipitated from isopropanol solution by dilution with hexane.

Kristenin is a useful antibiotic that possesses activity against various gram positive bacteria such as *Staphylococcus aureus*, and *Streptococcus pyogenes*. The antibiotic can be used to combat infections in various animal species due to various gram positive microorganisms such as those referred to above. The antibiotic is formulated according to conventional pharmaceutical practice in various dosage forms. For example, kristenin may be used in various animal species in an injectable dose of from about 20 to about 40 mg./kg./day.

EXAMPLE 1

(a) Yeast beef agar slants are seeded with *Bacillus subtilis* ATCC 31340. They are incubated 24–48 hours at 30° C. and then used to inoculate 100 ml of medium contained in 500 ml Erlenmeyer flasks. The composition of the germination medium is

|                          | grams |
|--------------------------|-------|
| Toasted nutrisoy flour   | 30.0  |
| Yeastamine               | 2.5   |
| Glucose                  | 50.0  |
| CaCO₃                    | 7.0   |
| Distilled water to 1000 ml. |    |

This medium is sterilized for 30 minutes at 121° C. and 15 lbs. steam pressure prior to use. The inoculated germination flasks are incubated at 25° C. for 72 hours on a rotary shaker, operating at 300 r.p.m. with a 2 inch throw.

A 4.5% (v/v) transfer is made from the germination flasks to a 14 liter glass vessel containing 10 liters of an aqueous soybean meal medium. The composition of this medium is the same as that used to prepare the germinators. The fermentation is carried out for 40 hours, at the end of which time the antibiotic is formed. The antibiotic is detected by conventional paper disc agar diffusion assay against *Staphylococcus aureus* FDA 209P. During incubation, the broth is aerated at the rate of 7 liters of air per minute at 5 p.s.i. During this period, the broth is agitated at the rate of 350 r.p.m. A broth dilution assay against this organism can also be used to follow antibiotic production.

(b) The fermentation broth from part (a) is centrifuged in a refrigerated centrifuge at 13,700× g to sediment the bacteria. The supernate (9.5 liters) is extracted twice with 3 liter portions of dichloroethane. The aqueous phase is adjusted to pH 7.5 and extracted twice with 3 liter portions of n-butanol. The combined butanol extracts are concentrated to dryness to give 25 g of an oily product. (c) The concentrate (25 g.) from part (b) is dissolved in 60 ml. of 30% methanol and stirred with 90 ml. of Amberlite CG-50 (H+) resin. The resin is then transferred to a column and eluted successively with 30% methanol (1750 ml.), 80% methanol, and finally with 1500 ml. of 0.1 N hydrochloric acid in 30% methanol. The bioactive fractions that are eluted with the latter solvent are located by paper disc-agar diffusion assay against *Staphylococcus aureus* 209P. The active fractions are pooled, concentrated in vacuo to remove methanol, adjusted to pH 7.7 with 2 N sodium hydroxide, and the resulting solution extracted four times with 100 ml. portions of n-butanol. The combined butanol extracts are washed with water and concentrated to dryness to yield 375 mg. of crude antibiotic as a tan amorphous powder.

(d) The 375 mg. of residue from part (c) is further purified by preparative thin layer silica gel chromatography using four 20×20 cm. plates (Quanta PQ 1F1000) developing with the upper phase of the solvent system n-butanol-acetic acid-water (8:1:10). The antibiotic appearing as a U.V. absorbing band (Rf=0.47) is scrapped off the plates, combined and eluted from the silica gel with the developing solvent. The eluate is concentrated to a small volume, diluted with water, and after adjustment of the pH to 7.5, the active material is extracted into n-butanol and concentrated to dryness yielding 192 mg. of residue.

(e) The 192 mg. sample from part (d) is dissolved in 80% methanol-water solution and applied to a Sephadex LH-20 column, 2.5 cm.×67 cm. The column is eluted with 0.5% acetic acid in 80% methanol-water. The fractions containing the bioactive component, as indicated by disc-agar diffusion assay, are combined and concentrated to dryness to yield 91.8 mgs. of purified kristenin.

EXAMPLE 2

To obtain the antibiotic kristenin in a highly pure form, a 20 mg. sample of antibiotic, prepared as in Example 1 (a) to (e), is chromatographed using the high performance liquid chromatographic technique (HPLC) on a ⅜″ by 3′ column of Porasil eluting with upper phase of the solvent system n-butanol-acetic acid-water (8:1:10) that contains an additional 10% by volume of n-butanol. The bioactive fractions are combined, concentrated to dryness and the residue precipitated from isopropanol solution with hexane to yield 15.4 mg. of pure kristenin as a white amorphous powder.

Elemental Analysis. Found: C, 56.58; H, 6.90; N, 9.92.

U.V. spectrum in methanol λmax 210 nm (27100), 247 nm (6090), 314 nm (4200) $[\alpha]_D^{MeOH} -81.9°$.

EXAMPLE 3

The peracetyl derivative of kristenin is prepared by dissolving 8.2 mg. of purified antibiotic, as obtained in Example 2, in 0.4 ml. of pyridine and 0.4 ml. of acetic anhydride and allowing the resulting solution to stand for 16 hrs. at 5° C. The solvents are removed in vacuo and the residue is purified by preparative TLC on silica gel developing with the solvent system chloroform-methanol (8:2). Kristenin-peracetate appeared as a fluorescent band that is eluted with the developing solvent. Concentration of the eluate yields 5.2 mg. of peracetyl derivative that crystallizes from isopropanol, m.p. 135°–141°.

U.V. spectrum in methanol: λ212 nm (16210), 236 nm (8637), 287 nm (2307).

A high resolution mass spectrum established the empirical formula.

Calcd. for $C_{26}H_{35}N_3O_{10}$: m/e 549.2322 Found: m/e 549.2323

EXAMPLE 4

Two fold broth dilution assays are done with several microorganisms. The antibiotic used in these assays is the pure material from Example 2.

| Organism | MIC (μg./ml.) |
|----------|---------------|
| *Staphylococcus aureus* FDA 209P | 3.1 |
| *Streptococcus pyogenes* C203 | 0.3 |
| *Escherichia coli* ATCC 10,536 | 37.5 |
| *Escherichia coli* SC 8294 | >50.0 |

What is claimed is:

1. The antibiotic kristenin having the infrared spectrum in KBr 3350, 2950, 1660, 1620, 1525, 1455, 1225, 1160, 1110, 805 and 690 cm$^{-1}$ shown in the FIGURE, the ultraviolet spectrum in methanol λmax 210 nm (27100), 247 nm (6090), 314 nm (4200), $[\alpha]_D^{methanol} -81.9°$, and the approximate elemental analysis C, 56.58, H, 6.90, and N, 9.92.

2. A process for producing the antibiotic kristenin as defined in claim 1 which comprises cultivating *Bacillus subtilis* ATCC 31340 in an aqueous nutrient medium containing an assimilable carbon and nitrogen source under submerged aerobic conditions at about 25° C. until substantial antibiotic activity is imparted to the medium and then extracting the antibiotic from the medium.

3. The process of claim 2 wherein the fermentation is carried out for from about 15 about 72 hours.

4. The process of claim 3 wherein the fermentation is carried out for about 40 hours.

* * * * *